(12) United States Patent
Nagabhushanam et al.

(10) Patent No.: US 9,737,502 B2
(45) Date of Patent: *Aug. 22, 2017

(54) CALEBIN A FOR HEPATIC STEATOSIS

(71) Applicants: Kalyanam Nagabhushanam, East Windsor, NJ (US); Anju Majeed, East Windsor, NJ (US); Muhammed Majeed, Edison, NJ (US)

(72) Inventors: Kalyanam Nagabhushanam, East Windsor, NJ (US); Anju Majeed, East Windsor, NJ (US); Muhammed Majeed, Edison, NJ (US)

(73) Assignee: SAMI LABS LIMITED, Bangalore (IN)

( * ) Notice: Subject to any disclaimer, the term of this patent is extended or adjusted under 35 U.S.C. 154(b) by 0 days.

This patent is subject to a terminal disclaimer.

(21) Appl. No.: 14/690,438

(22) Filed: Apr. 19, 2015

(65) Prior Publication Data
US 2016/0199340 A1    Jul. 14, 2016

Related U.S. Application Data

(63) Continuation-in-part of application No. 14/274,096, filed on May 9, 2014, now Pat. No. 9,328,330, which is a continuation-in-part of application No. 13/347,071, filed on Jan. 10, 2012, now Pat. No. 8,933,121.

(60) Provisional application No. 61/431,147, filed on Jan. 10, 2011.

(51) Int. Cl.
*A61K 31/235* (2006.01)
*C12N 5/077* (2010.01)

(52) U.S. Cl.
CPC .......... *A61K 31/235* (2013.01); *C12N 5/0653* (2013.01); *C12N 2500/76* (2013.01)

(58) Field of Classification Search
CPC .................................................. A61K 31/235
See application file for complete search history.

(56) References Cited

U.S. PATENT DOCUMENTS

2006/0148905 A1* 7/2006 Kim ................ A61K 31/12
514/679
2008/0280976 A1* 11/2008 Jin ................ A23L 1/3002
514/469

* cited by examiner

*Primary Examiner* — Craig Ricci
*Assistant Examiner* — Christopher R Stone

(57) ABSTRACT

The present invention discloses the potential of Calebin A in attenuating high fat diet (HFD) induced hepatic steatosis in mammals.

2 Claims, 15 Drawing Sheets
(4 of 15 Drawing Sheet(s) Filed in Color)

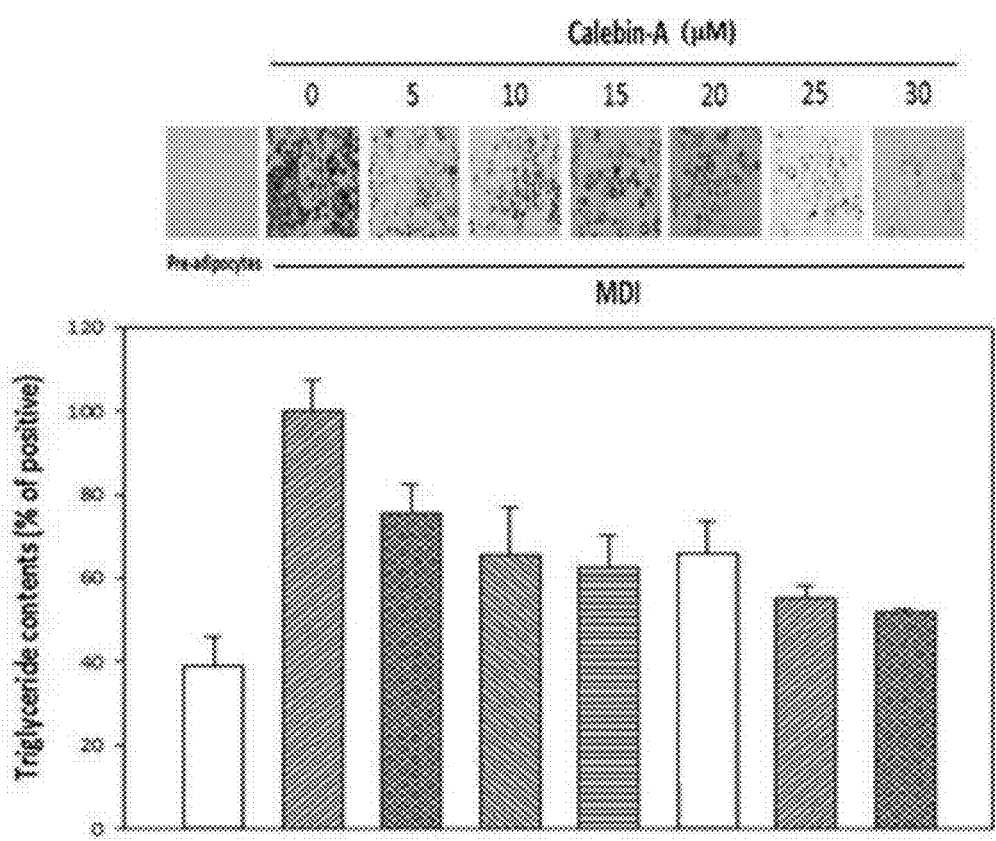

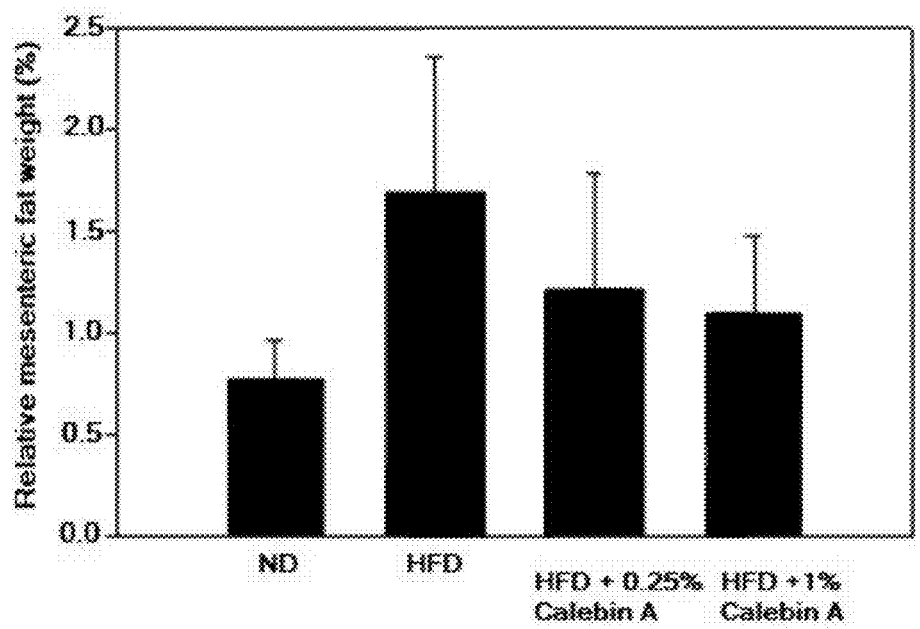

CALEBIN A FOR HEPATIC STEATOSIS

CROSS REFERENCE TO RELATED APPLICATIONS

This application is a continuation-in-part patent application of co-pending U.S. patent application Ser. No. 14/274,096 filed on 9 May 2014 which in turn is a continuation-in-part patent application of Ser. No. 13/347,071 filed on 10 Jan. 2012 and granted as U.S. Pat. No. 8,933,121 on 13 Jan. 2015, which in turn is the non-provisional filing of provisional application 61/431,147 filed on Jan. 10, 2011.

FIELD OF INVENTION

The invention in general relates to medicaments for obesity management. More specifically, it relates to anti-obesity potential of Calebin A in terms of its ability to cause lipolysis in well differentiated adipocytes. Also disclosed is the ability of Calebin A to decrease a high fat induced hepatic steatosis in mammals.

DESCRIPTION OF PRIOR ART

Obesity is the most prevalent nutritional disorder in industrialized countries and is a growing problem in developing countries. It is described as a global epidemic and overweight and obese individuals (BMI of 25 and above) are at increased risk for various chronic physical ailments and psychological problems such as depression, eating disorders and low self esteem. It is associated with various diseases like cardiovascular diseases, diabetes mellitus, osteoarthritis, obstructive sleep apnea and cancer. WHO considers obesity to be one of the top 10 causes of preventable death worldwide.

In obesity, there is an increase in the adipose tissue mass due to the production of new fat cells (adipocytes) through the process of adipogenesis and/or the deposition of increased amounts of cytoplasmic triglyceride per cell. A fat cell develops as internally produced lipid droplets coalesce into a single large mass. Eventually, cellulite results due to enhanced adipogenesis and accumulation of chunks of adipocytes under the skin dermis.

Studies of adipogenesis have proceeded with the hope that manipulation of this process in humans might lead to a reduction in the burden of obesity and diabetes. At molecular level, several markers have been targeted in treating obesity such as leptin, adiponectin, TNF-α etc Though drugs are available for treating the disorder, there is a constant need and search for safe natural approach to help manage obesity and its related socio-economic consequences.

Calebin A is known to protect neuronal cells from β-amyloid insult (Park S Y et al, J Nat Prod. 2002 September; 65(9):1227-31), induce apoptosis and modulate MAPK family activity in drug resistant human gastric cancer cells (Li Y et al, Eur J. Pharmacol. 2008 Sep. 4; 591(1-3):252-8). Zeng Y et al. (Chem Pharm Bull (Tokyo) 2007 June; 55(6):940-3) discusses two new calebin derivatives, 4"-(4'''-hydroxyphenyl-3'''-methoxy)-2"-oxo-3"-butenyl-3-(4'-hydroxyphenyl)-propenoate and 4"-(4'''-hydroxyphenyl)-2"-oxo-3"-butenyl-3-(4'-hydroxyphenyl-3'-methoxy)-propenoate.

The present invention discloses the potential of Calebin A to prevent fat accumulation during the terminal differentiation of adipocytes (fat cells) and applications thereof in obesity management. The present invention elucidates the potential of Calebin A to favorably modulate biochemical markers associated with obesity. Notable biomodulatory properties of Calebin A include inhibiting leptin production, increasing adiponectin expression and inhibiting local (adipocyte) and systemic inflammation caused by pro-inflammatory cytokines Tumor Necrosis Factor (TNF-α), Interleukin-6 (IL-6) and Interleukin-1 (IL-1β).

Accordingly, it is the principle objective of the present invention to disclose anti-obesity potential of Calebin A. It is another objective of the present invention to disclose the ability of Calebin A to induce lipolysis in well differentiated adipocytes. It is yet another objective of the present invention to also disclose the ability of Calebin A to decrease high fat diet induced hepatic steatosis in mammals.

The invention fulfills the aforesaid objectives and provides further related advantages

SUMMARY OF THE INVENTION

The present invention discloses the potential of Calebin A in inhibiting adipogenesis and applications thereof in obesity management. The present invention elucidates the potential of Calebin A to favorably modulate biochemical markers associated with obesity in mammals. Notable biomodulatory properties of Calebin A include inhibiting leptin production, increasing adiponectin expression and inhibiting local (adipocyte) and systemic inflammation caused by pro-inflammatory cytokines Tumor Necrosis Factor (TNF-α), Interleukin-6 (IL-6) and Interleukin-1 (IL-1β). Also disclosed as part of the present invention is the ability of Calebin A to stimulate lipolysis in fully differentiated adipocytes. Further, the present invention also discloses the ability of Calebin A to decrease high fat diet induced hepatic steatosis in mammals.

Other features and advantages of the present invention will become apparent from the following more detailed description, taken in conjunction with the accompanying drawings, which illustrate, by way of example, the principle of the invention.

BRIEF DESCRIPTION OF FIGURES

The patent or application filed contains at least one drawing executed in color. Copies of this patent or patent application, publication with color drawing (s) will be provided by the office upon request and payment of the necessary fee.

FIG. 8 shows that Calebin A inhibits differentiation and adipogenesis of 3T3-L1 preadipocytes.

FIG. 14 (C) shows the same results graphically.

DETAILED DESCRIPTION OF THE INVENTION

The present invention discloses the potential of Calebin A to prevent fat accumulation during the terminal differentiation of adipocytes (fat cells) and applications thereof in obesity management. The present invention elucidates the potential of Calebin A to favorably modulate biochemical markers associated with obesity. Notable biomodulatory properties of Calebin A include inhibiting leptin production, increasing adiponectin expression and inhibiting local (adipocyte) and systemic inflammation caused by pro-inflammatory cytokines Tumor Necrosis Factor (TNF-α), Interleukin-6 (IL-6) and Interleukin-1 (IL-1β).

Figure 1:
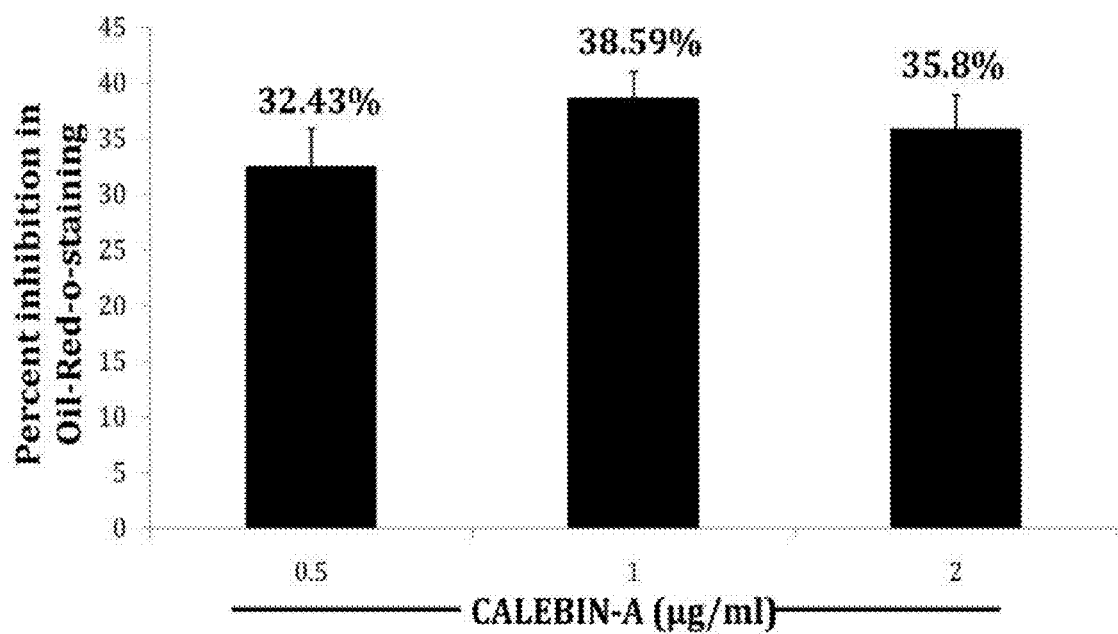
FIG. 1 shows the graphical representation of the percentage adipogenesis inhibition effected by Calebin A at concentrations of 0.5, 1.0 and 2.0 µg/ml as studied by the Oil-Red-O-Staining method.

In the most preferred embodiment, the present invention relates to a method of inhibiting adipogenesis, said method comprising step of bringing into contact the adipocytes with an effective amount of Calebin A. In other words, the present invention relates to a method of preventing accumulation of fat during the terminal differentiation of mammalian adipocytes. (FIGS. 1 and 8).

Figure 2:
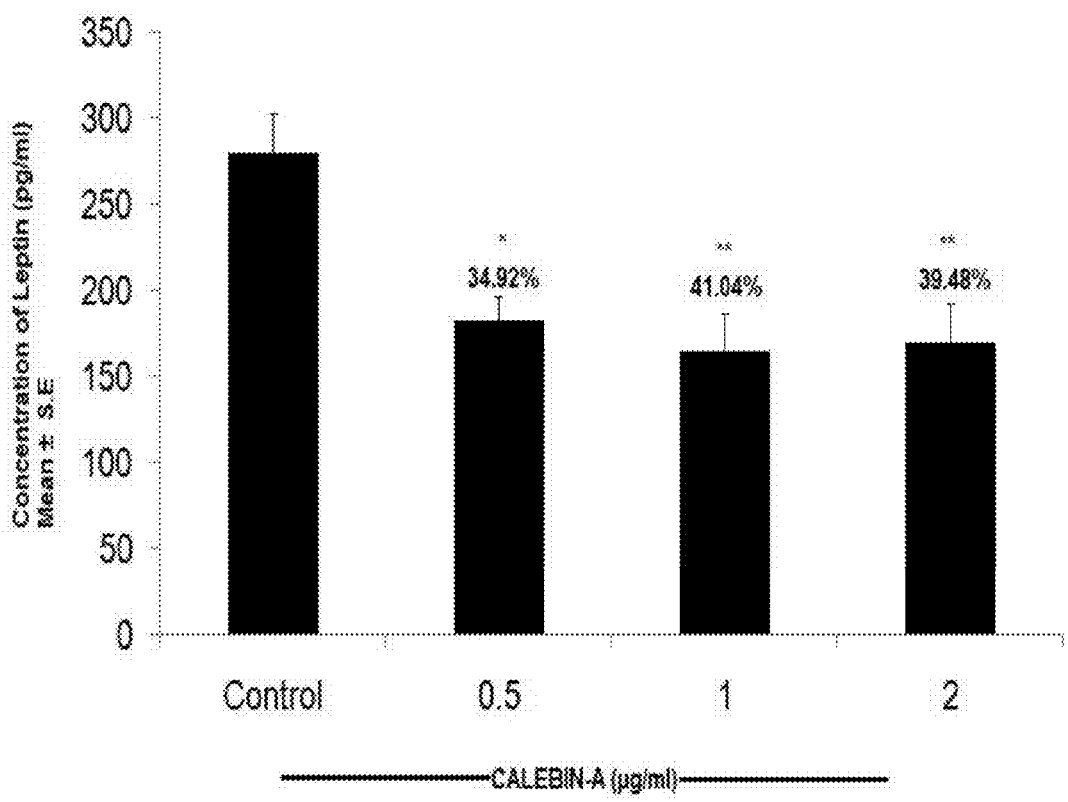
FIG. 2 shows the graphical representation of the percentage inhibition of leptin production in human adipocytes effected by Calebin A at concentrations of 0.5, 1.0 and 2.0 µg/ml. P value *:<0.01; **:<0.001.

In another preferred embodiment, the present invention relates to a method of inhibiting leptin expression in adipocytes, said method comprising step of bringing into contact the adipocytes with an effective amount of Calebin A (FIG. 2).

Figure 3:
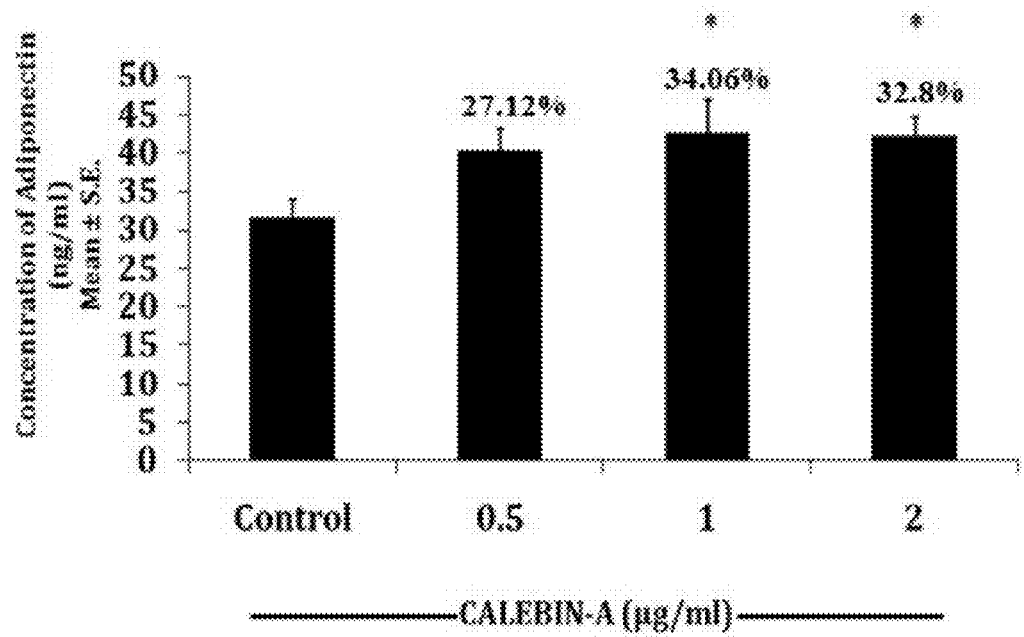
FIG. 3 shows the graphical representation of the percentage increase of adiponectin expression in human adipocytes effected by Calebin A at concentrations of 0.5, 1.0 and 2.0 µg/ml. P value *:<0.01.

In another preferred embodiment, the present invention relates to a method of increasing expression of adiponectin in adipocytes, said method comprising step of bringing into contact the adipocytes with an effective amount of Calebin A (FIG. 3).

Figure 4:
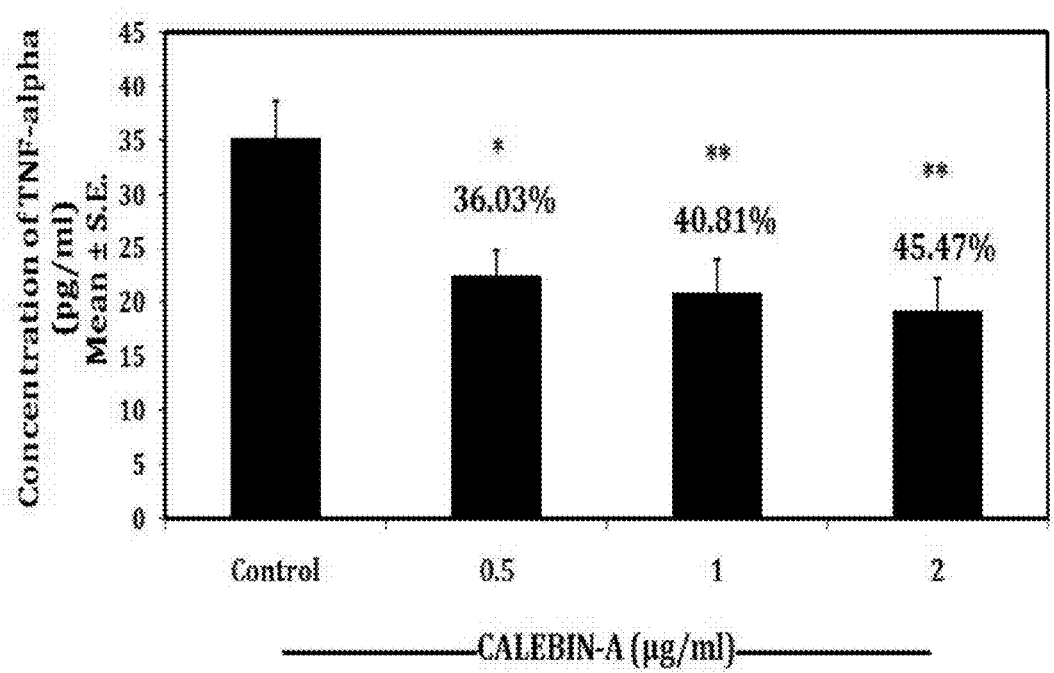
FIG. 4 shows the graphical representation of the percentage inhibition of TNF-α expression (P value *:<0.01; **:<0.001) in human adipocytes effected by Calebin A at concentrations of 0.5, 1.0 and 2.0 µg/ml.

In another preferred embodiment, the present invention relates to a method of inhibiting pro-inflammatory cytokine TNF-α expression in adipocytes, said method comprising step of bringing into contact the adipocytes with an effective amount of Calebin A (FIG. 4).

Figure 5:
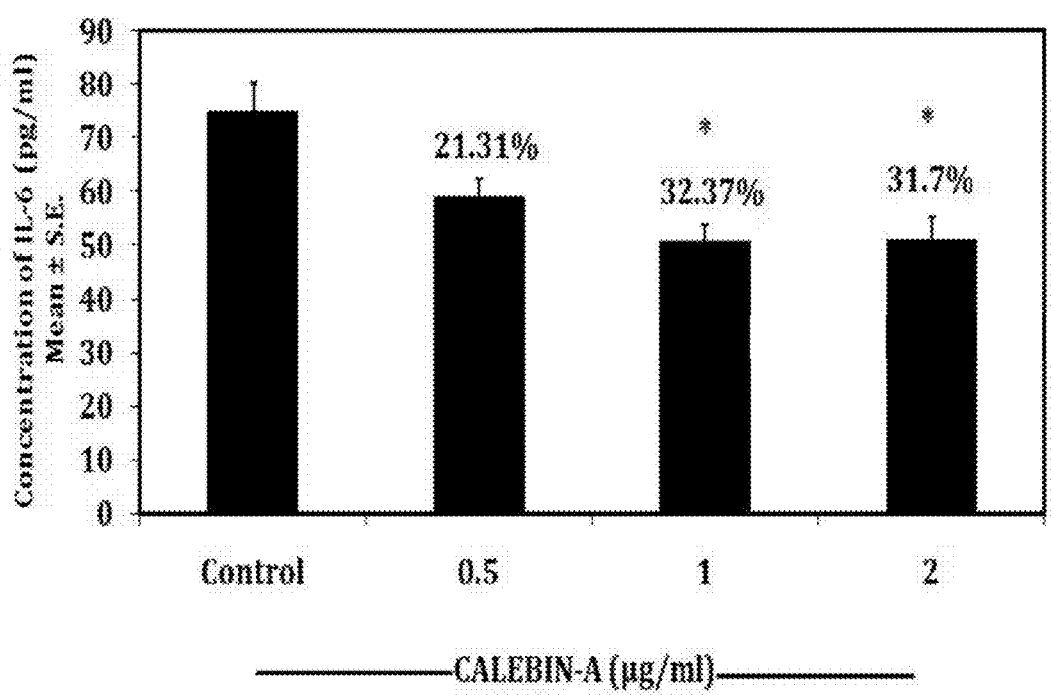
FIG. 5 shows the graphical representation of IL-6 expression (P value *:<0.01) respectively, in human adipocytes effected by Calebin A at concentrations of 0.5, 1.0 and 2.0 µg/ml.

In yet another preferred embodiment, the present invention relates to a method of inhibiting pro-inflammatory cytokine Interleukin-6 expression in adipocytes, said method comprising step of bringing into contact the adipocytes with an effective amount of Calebin A (FIG. 5).

In specific embodiment, the adipocytes referred to herein above are human adipocytes.

In yet another preferred embodiment, the present invention relates to a method of reducing obesity induced systemic expression of pro-inflammatory cytokines in mammals, said method comprising step of administering an effective amount of Calebin A to a subject in need thereof. In specific embodiments, the pro-inflammatory cytokines referred to herein in this paragraph include Tumor Necrosis Factor-α (TNF-α), Interleukin-6 (IL-6) and Interleukin-1β (IL-1β) [FIGS. 6 and 7].

In yet other most preferred embodiments, the present invention relates to
1. A method of obesity management in mammals with risk of excessive accumulation of body fat, said method comprising the step of dietary oral supplementation of effective amounts of Calebin A to said mammals to bring about the effect of adipogenesis inhibition.
2. Use of Calebin A in the management of obesity in mammals with risk of excessive accumulation of body fat, said use comprising the step of dietary oral supplementation of effective amounts of Calebin A to said mammals to bring about the effect of adipogenesis inhibition.
3. A method of inhibiting adipogenesis in mammals with risk of excessive accumulation of body fat, said method comprising the step of dietary oral supplementation of effective amounts of Calebin A to said mammals.
4. A method of reducing body weight of obese mammals, said method comprising step of orally administering effective amounts of Calebin A to said mammals.
5. Use of Calebin A in a method to reduce body weight in obese mammals, said use comprising step of orally administering effective amounts of Calebin A to said mammals.
6. A method of increasing systemic expression of adiponectin in obese mammals, said method comprising step of dietary oral supplementation of effective amounts of Calebin A to said mammals.
7. A method for aiding in preventing, delaying the onset of and/or slowing the progression of diabetes mellitus Type II in an obese mammal, said method comprising step of orally administering therapeutically effective amounts of Calebin A to said mammal to achieve an increase in systemic adiponectin expression levels.
8. A method of treating obesity in mammals, said method comprising the step of dietary oral supplementation of effective amounts of Calebin A to said mammals to bring about the effects of adipogenesis inhibition, reduction in body weight and increased systemic expression of adiponectin.
9. A method of promoting lean body mass in a mammal, said method comprising the step of dietary oral supplementation of effective amounts of Calebin A to said mammals to bring about effect of increase in lean body mass by shifting the proportion between lean body mass and adipose tissue in favor of lean body mass.

In yet another preferred embodiment, the subject is a mammal.

In yet another preferred embodiment, the subject is a human.

The potential therapeutic value of Calebin A as an anti-obesity molecule may be understood through specific examples elucidated herein below.

Example I

Acute Oral Toxicity of Calebin A

Table I lists the parameters studied for Acute Oral Toxicity of Calebin A.

Results:

No mortality was observed up to 2000 mg/kg p.o. in mice up to two weeks of observation.

TABLE I

Parameters studied for Acute Oral Toxicity of Calebin A

| General Behaviour | Dermal |
| --- | --- |
| Aggression = Nil | Blanching = Nil |
| Fear = Nil | Hyperaemia = Nil |
| Passive = Nil | Cyanosis = Nil |
| General Movement = Normal | |
| General Locomotor Activity = Normal | |

| Central Nervous System | General Parameters |
| --- | --- |
| Excitation = Nil | Muscular Weakness = Nil |
| Motor Activity = Nil | Salivation = Nil |
| Tremors = Nil | Pilo Erection = Nil |
| Clonic Convulsions = Nil | Diarrhea = Nil |
| Tonic Convulsion = Nil | |

| Respiratory System | Reflexes |
| --- | --- |
| Respiration Rate = Normal | Corneal = No effect |
| Respiration Depth = Normal | Pinnal = No effect |

| Autonomic Nervous System | Food and Water (Intake and Excretion) |
| --- | --- |
| Motor Activity = Normal | Fecal Output = Normal |
| Atexia = Nil | Urine Output = Normal |
| Respiration Rate = Normal | |
| Diarrhea = Nil | |

Example II

Oil Red-O-Staining of Adipogenic Cultures and Estimation of Leptin, Adiponectin, TNF-α and IL-6 by ELISA Terminal differentiation of adipocytes is accompanied by the accumulation of great amounts of lipids in large cytoplasmic vesicles. A common assay to measure adipocyte differentiation in cell culture is with the dye Oil Red-O (ORO). ORO is a lipid-soluble bright red dye which is a reliable indicator of adipocyte differentiation (adipogenesis).

Principle:

Oil Red-O (Solvent Red 27, Sudan Red SB, C.I. 26125, and $C_{26}H_{24}N_4O$) is a lysochrome (fat-soluble dye) diazo dye used for staining of neutral triglycerides and lipids on frozen sections and some lipoproteins on paraffin sections. It has the appearance of a red powder with maximum absorption at 518(359) nm. Oil Red-O is one of the dyes used for Sudan staining. Similar dyes include Sudan III, Sudan IV, and Sudan Black B. The staining has to be performed on fresh samples, as alcohol fixation removes the lipids. Oil Red O largely replaced Sudan III and Sudan IV, as it provides much deeper red color and the stains are therefore much easier to see.

Oil Red-O is an oil soluble dye. Oil soluble dyes exhibit greater solubility of the dye in lipid substances in the tissues/cells, than in the usual hydro alcoholic dye solvents. Hence, it will deeply stain the cells.

Methodology:

3T3-L1 cells approximately 60×10⁴ cells are seeded for 48-72 hrs to get 70-80% confluence. After 48 hrs 200 μl of AIM (Adipogenesis induction medium) freshly prepared is added. 72 hrs later 200 μl APM (Adipogenesis progression medium) with the test compounds in different concentrations is added to the wells. The cells are incubated for 48 hrs in a humidified atmosphere (37° C.) of 5% CO2 and 95% air. The supernatant is collected and stored for the estimation of leptin, adiponectin, IL-6 and TNF-α by ELISA. Cells are fixed by adding 100 μl of 10% formalin and ORO staining is done. OD is read at 492 nm in microplate reader. The results are expressed as $IC_{50}$ values using Graphpad prism software.

The percentage of inhibition of adipogenesis is calculated as follows, $$\% \text{ inhibition} = C - T/T * 100$$

Where C-absorbance of Oil red 0 in differentiating/undifferentiated cells

T-absorbance of Oil Red-O in sample treated differentiating/undifferentiated cells. The estimation of leptin, adiponectin, IL-6 and TNF-α is done according to user's manual from R&D Systems.

REFERENCES

1. Wa Z, Xie Y, Morrison R F, Bucher N L R, Farmer S R 1998. PPAR γ induces the Insulin-dependent Glucose Transporter GLUT4 in the absence of C/EBP☐ during the conversion of 3T3 fibroblasts into adipocytes. J Clin Invest. 101:22-32.
2. A pre-adipose 3T3 cell variant highly sensitive to adipogenic factors & to human growth hormone. L A Salazar-Olivo, F Castro-Munozledo & W Kuri-Harcuch. Department of Cell Biology, Centro de Investigation y de Estudios Avanzados del L.P.N., Mexico D.F., Mexico. Journal of Cell Science, 1995. Vol 108, Issue 5 2101-2107.
3. A Nuclear Receptor Atlas: 3T3-L1 Adipogenesis. Mingui Fu, Tingwan Sun, Angie L. Bookout, Micheal Downes, Ruth T. Yu, Ronald M. Evans and David J. Mangelsdorf. Molecular Endocrinology, 2005. 19 (10): 2437-2450.
4. "Expression of a Constitutively Active Akt Ser/Thr Kinase in 3T3-L1 Adipocytes Stimulates Glucose Uptake and Glucose Transporter 4 Translocation, Aimee D Kohn et al, J. Biol. Chem. 1996, 271:31372-31378.

Result:

FIG. 1 shows percentage adipogenesis inhibition of 32.43%, 38.59% and 35.8% respectively effected by Calebin A at concentrations of 0.5, 1.0 and 2.0 μg/ml studied by the Oil-Red-O-Staining method.

FIG. 2 shows percentage inhibition of leptin production (34.92%, 41.04% and 39.48% respectively) in human adipocytes by Calebin A at concentrations of 0.5, 1.0 and 2.0 μg/ml. The importance of the effects of Calebin A in inhibiting leptin production in human adipocytes and correlation thereof to obesity management stems from the following facts (Notes on Pathophysiology of the Endocrine System. Colorado State University).

Leptin is a protein hormone expressed predominantly in adipocytes. It has important effects in regulating body weight, metabolism and reproductive function. Encoded by the obese (ob) gene, the protein is approximately ~16 kDa in mass. At normal concentrations, leptin's biological function is predominantly vested in its effects on hypothalamic centers of the brain that control hunger, appetite, regulation of body temperature and energy metabolism. Thus leptin, in a non-obese individual could result in weight loss by two important mechanisms. (i) Decrease in hunger and food consumption most probably through the inhibition of neuropeptide Y that controls feeding behavior and (ii) increase in energy expenditure through increased body temperature, oxygen consumption and loss of adipose tissue mass. However, excessive secretion of leptin as in case of obesity or experimental models of induced obesity leads to disrupted functions of hypothalamic centers that an obese subject fails to attain satiations and tends to go on a over feeding mode. Hence it becomes imperative to bring about effective reduction of the over excessive levels of leptin in obesity and Calebin A shows promise in this area as indicated in FIG. 2.

FIG. 3 shows percentage enhancement of adiponectin expression (27.12%, 34.06% and 32.8% respectively) in human adipocytes by Calebin A at concentrations of 0.5, 1.0 and 2.0 µg/ml. Adiponectin is a cytokine produced almost exclusively by adipocytes and is expressed in very high levels by lean and healthy individuals. Obese individuals on the other hand express reduced levels of this adipokine and are prone to coronary heart disease (CAD), diabetes mellitus and hypertension.

REFERENCES

1. Tamar. R. Aprahamian and Flora Sam, "Adiponectin in Cardiovascular Inflammation and Obesity, Int J. Inflam. 2011; 2011: 376909;
2. Hotta K. Funahashi T, Arita Y, et al. Plasma concentrations of a novel, adipose-specific protein, adiponectin, in type 2 diabetic patients. Arteriosclerosis, Thrombosis and Vascular Biology. 2000; 20(6):1595-1599;
3. Iwashima Y, Katsuya T, Ishikawa K, et al. Hypoadiponectinemia is an independent risk factor for hypertension. Hypertension. 2004; 43(6):1318-1323;
4. Kumada M, Kihara S, Sumitsuji S, et al. Association of hypoadiponectinemia with coronary artery disease in men. Arteriosclerosis, Thrombosis and Vascular Biology. 2003; 23(1):85-89 and
5. Lindsay R S, Funahashi T, Hanson R L, et al. Adiponectin and development of type 2 diabetes in the Pima Indian population. The Lancet. 2002; 360(9326):57-58.

Calebin A is shown (FIG. 3) to effectively increase levels of adiponectin in human adipocytes and thus show promise in the area of obesity management.

FIGS. 4 and 5 show the percentage inhibition of TNF-α (36.03%, 40.81% and 45.47% respectively) and IL-6 (21.31%, 32.37% and 31.7% respectively) by Calebin A at concentrations of 0.5, 1.0 and 2.0 µg/ml. Bastard J P et al, "Recent Advances in the relationship between obesity, inflammation and insulin resistance", Eur Cytokine Netw. 2006 March; 17(1):4-12 cite that obesity is associated with low-grade inflammation of the white adipose tissue (WAT). The authors also remark that in obesity, WAT is characterized by increased expression of pro-inflammatory molecules like TNF-α and IL-6 which not only exert effects on WAT but also on other systemic organs of the body. FIGS. 4 and 5 demonstrate that Calebin A is effective in reducing TNF-α and IL-6 expression in adipocytes and would be a useful agent to modulate effects of local and systemic inflammation in obesity.

Example III

Modulation of Systemic Inflammation by Calebin A

The present inventors also adduce extra evidence to support the ability of Calebin A to suppress intracellular TNF and extracellular IL-1β in murine neutrophil systems (Table II, Table III). Neutrophils are isolated by histopaque gradient method tested for their ability to produce in vitro TNF-α following stimulation with Lipopolysaccharide (LPS). The cells were incubated with phycoerythrin (PE)-labeled anti-mouse TNF-α in the dark, and after being washed with sterile PBS, samples were resuspended in PBS (pH 7.4) and acquired directly on the flow cytometer (BDLSR; Becton Dickinson). A fluorescence trigger was set on the PE (FL1) parameter of the gated neutrophil populations (10,000 events). Rolipram at 100 µg/ml was used as standard inhibitor of TNF-α in this study. Fluorescence compensation, data analysis, and data presentation were performed using Cell Quest Pro software (Becton Dickinson).

REFERENCES

1. Clara, B., R. C. Arancha, G. M. Andre's, P. Atanasio, A. Julia, and O. Alberto. 2003. A new method for detecting TNF-α-secreting cells using direct immunofluorescence surface membrane stainings. J. Immuno. Methods 264: 77-87.
2. Khurshid A. Bhat, Bhahwal A. Shah, Kuldeep K. Gupta, Anjali Pandey, Sarang Bani, Subhash C. Taneja. Semisynthetic analogs of pinitol as potential inhibitors of TNF-α cytokine expression in human neutrophils. Bioorganic & Medicinal Chemistry Letters 19 2009, 1939-1943.

TABLE II

| Serial No | Sample | Concentration (µg/ml) | Expression of TNF-α Mean ± S.E | % Activity |
|---|---|---|---|---|
| 1 | LPS Control | — | 2.62 ± 0.01 | — |
| 2 | Calebin A | 0.5 | 1.87 ± 0.04* | 28.62%↓ |
| 3 | Calebin A | 1.0 | 1.70 ± 0.02** | 35.11%↓ |
| 4 | Calebin A | 2.0 | 1.59 ± 0.05** | 39.31%↓ |
| 5 | Rolipram | 100 | 0.73 ± 0.09** | 72.13%↓ |

%↓: indicates suppression of TNF-α expression
No. of observations = 3
P-value:
*<0.01;
**<0.001 students 't' test % ↓: indicates suppression of TNF-α expression No. of observations=3

P-value: *<0.01; **<0.001 students 't' test

TABLE III

| Samples Treatment | Concentration (pg/ml) | % Activity |
|---|---|---|
| LPS Control | 51.80 ± 2.18 | — |
| Calebin A | | |
| 0.5 µg/ml | 41.24 ± 1.16* | 20.38%↓ |
| 1.0 µg/ml | 39.26 ± 2.52* | 24.20%↓ |
| 2.0 µg/ml | 37.16 ± 2.11** | 28.26%↓ |
| Rolipram Standard | | |
| 100 µg/ml | 22.52 ± 1.60** | 56.52%↓ |

%↓: indicates suppression of IL-1 β expression
No. of observations = 3
P-value:
*<0.01;
**<0.001 students 't' test % ↓: indicates suppression of IL-1β expression No. of observations=3

P-value: *<0.01; **<0.001 students 't' test

Figure 6:
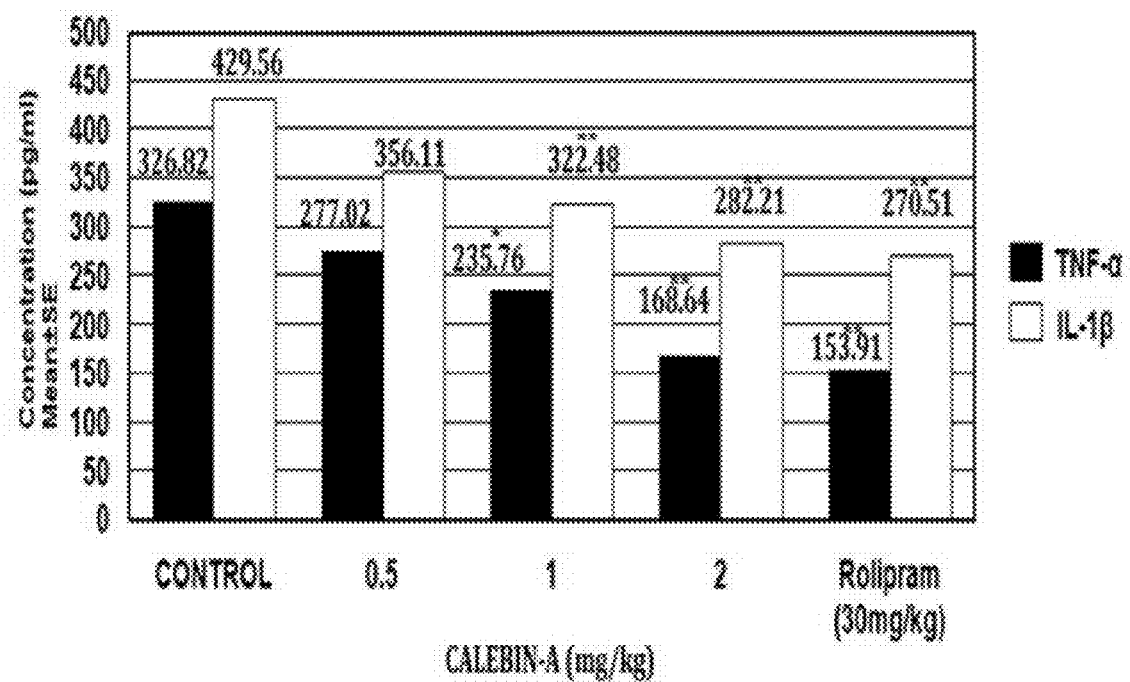
FIG. 6 shows the graphical representation of the effect of multiple dose of Calebin A on the expression of TNF-α and IL-1β in the serum from treated Swiss Albino mice. No. of animals=6 per group, P-value: *<0.01; **<0.001 students 't' test.
Figure 7:
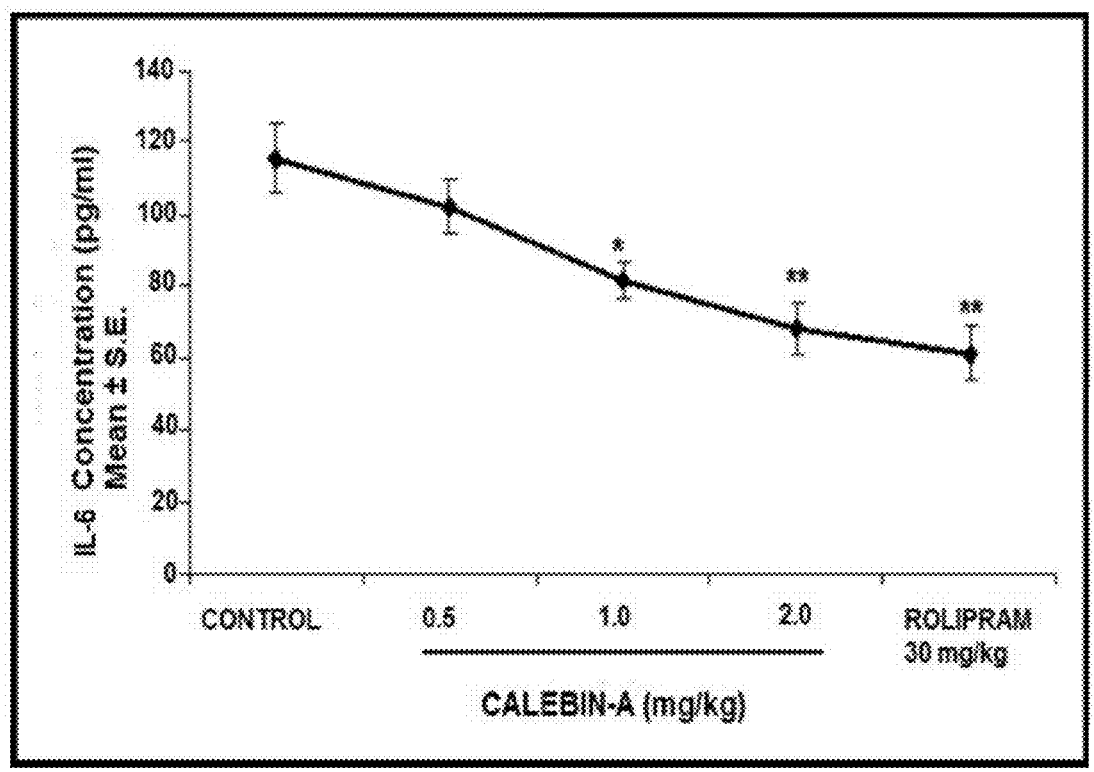
FIG. 7 shows the graphical representation of the effect of multiple dose of Calebin A on the expression of IL-6 in the serum from treated Swiss Albino mice. No. of animals=6 per group, P-value:*<0.01; **<0.001 students 't' test.

The present inventors also adduce study data on the ability of Calebin A to reduce expression of Extracellular TNF-α, IL-1 beta [FIG. 6] and IL-6 [FIG. 7] in serum from treated mice (in-vivo models). Swiss albino male mice aged 6-8 weeks were maintained at 22±2° C. under 12/12 h light dark cycle. Mice received oral treatment of test drugs at graded doses (w/v) for 6 days, followed by intravenous injection of 1 mg/kg of LPS according to the method described by Brieva A, Guerrero A, Alonso-Lebrero J L and Pivel J P. 2001. Immunoferon, a glycoconjugate of natural origin, inhibits LPS-induced TNF-α production and inflammatory responses. International Immunopharmacology 1, 1979-1987. Six mice were employed in each group and experiments were performed in triplicates. TNF-α, IL-1 beta and IL-6 production was evaluated by a commercial ELISA kits (R&D Systems) in serum from treated mice, 90 min after LPS injection. Rolipram at 30 mg/kg was used as standard drug.

FIGS. 6 and 7 demonstrate that Calebin A is effective in reducing TNF-α, IL-1 beta and IL-6 thus indicating that the compound is a useful agent to modulate effects of local and systemic inflammation in obesity.

Example IV

Adipogenesis Inhibition by Calebin A

Cell Culture and Adipocyte Differentiation

Mouse 3T3-L1 pre-adipocytes purchased from the American Type Culture Collection (Rockville, Md.) were grown in Dulbecco's Modified Eagle's Medium (DMEM) supplemented with 2 mM glutamine (GIBCO BRL), 1% penicillin/streptomycin (10000 units of penicillin/mL and 10 mg streptomycin/mL) and 10% fetal calf serum (FCS) at 37° C. under a humidified 5% CO2 atmosphere. Briefly, cells were seeded into 24-well ($2 \times 10^4$/mL) or 10 cm dish with DMEM containing 10% fetal bovine serum (FBS) to full confluence. Two days after confluence (defined as day 0), cells were incubated in differentiation medium (MDI) containing 1.7 µM insulin, 0.5 mM 3-isobutylmethylxanthine (IBMX) and 12.7 µM dexamethasone (DEX) in DMEM containing 10% FBS for 2 days. The medium was then replaced by DMEM containing 10% FBS and insulin (1.7 µM) with or without Calebin A which was replaced every 2 days. The final concentrations of dimethyl sulfoxide (DMSO) in the culture medium were <0.05%. The cells were harvested after 8 days (at day 10) for Oil Red O staining.

Oil Red-O Staining

At the end of differentiation, cells were washed twice with phosphate-buffered saline (PBS), fixed with 10% formalin for 60 min, stained with 0.5% Oil Red O in isopropanol for 1 h at room temperature. Excess Oil Red-O dye was washed twice with distilled water and then dried. The stained lipid droplets within cells were visualized by light microscope and photographed with a digital camera at 100× magnification. To quantify lipid accumulation, the stained lipid droplets were dissolved in isopropanol and the absorbance was measured at 520 nm.

FIG. 8 shows that Calebin A inhibits differentiation and adipogenesis of 3T3-L1 preadipocytes. Differentiation of 3T3-L1 preadipocytes stained with Oil Red O and photographed (upper and middle). 3T3-L1 preadipocytes were incubated with MDI (DMEM with IBMX, DEX, and insulin) for 2 days and then replaced with DMEM containing insulin with or without Calebin A (0, 5, 10, 15, 20, 25 and 30 µM), respectively, for 8 days, Lipid content was extracted from Oil Red O stained cells by 2-propanol and quantified by spectrophotometric analysis at 520 nm.

Animal Experiment—Study I

Figure 9A:
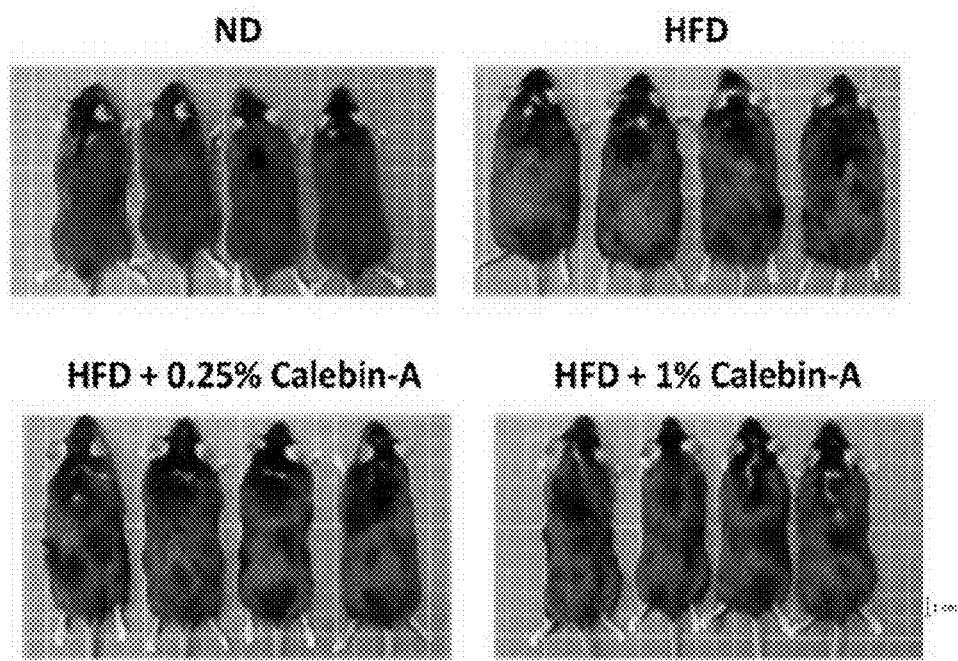
FIG. 9 (A) and FIG. 9(B) respectively show the photographs and graphical representation of the effects of diet supplementation on the body weights of experimental groups of C57BL/6 mice.
Figure 9:
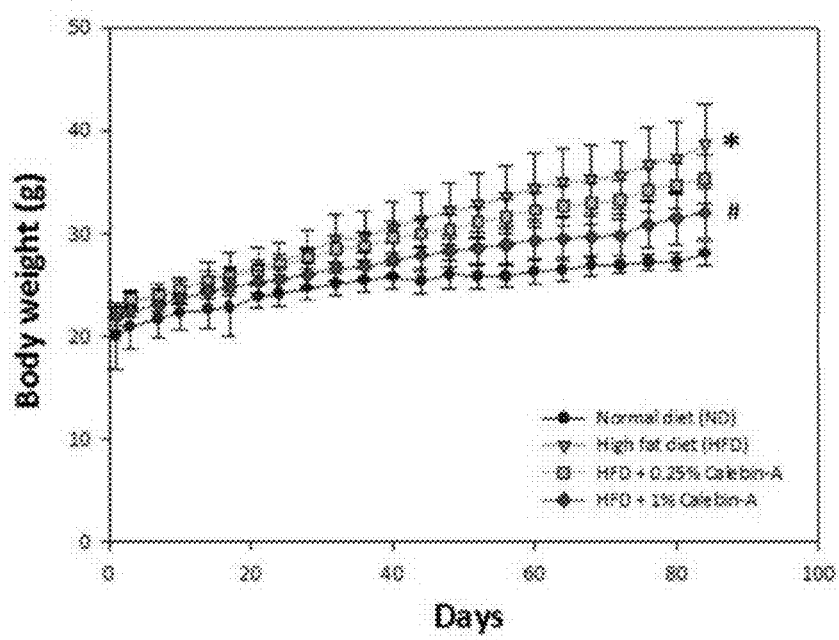

Male C57BL/6J mice at 5 weeks of age were purchased from the BioLASCO Experimental Animal Center (Taiwan Co., Ltd., Taipei, Taiwan) and housed in a controlled atmosphere (25±1° C. at 50% relative humidity) and with a 12-h light/12-h dark cycle. After 1 week of acclimation, animals were randomly distributed into four groups of 8 animals each as follows: normal diet (ND, 15% energy as fat), high fat diet (HFD; 40% energy as fat), and HFD supplemented with 0.25% or 1% Calebin A (2.5 g or 10 g Calebin A/kg diet), respectively, for 12 weeks (Table V). The experimental diets were modified from the Purina 5001 diet (LabDiet, PMI Nutrition International) and the composition is listed in Table IV. Animals had free access to food and water at all times. Food cups were replenished with fresh diet daily. The diet intake of animals was monitored every day and the body weight was recorded weekly. All animal experimental protocol used in this study was approved by Institutional Animal Care and Use Committee of the National Kaohsiung Marine University (IACUC, NKMU). At the end of the study, all animals were fasted overnight and sacrificed by $CO_2$ asphyxiation. Blood samples were collected from the heart for biochemical analysis. Liver, spleen, kidney and fat pads (perigonadal, retroperitoneal and mesenteric fat) were immediately removed, weighed (TABLE VI) and photographed. FIG. 9 (A) shows the representative photographs of each group at the end of week 12. Body weight was monitored weekly, and the average body weight of each group was expressed as the mean±SE. Statistical analysis was done by Student's t test. (*) P<0.01, compared with ND group; (#) P<0.01, compared with HFD group. ND, normal diet and HFD, high-fat diet (FIG. 9 (B)).

Figure 10:
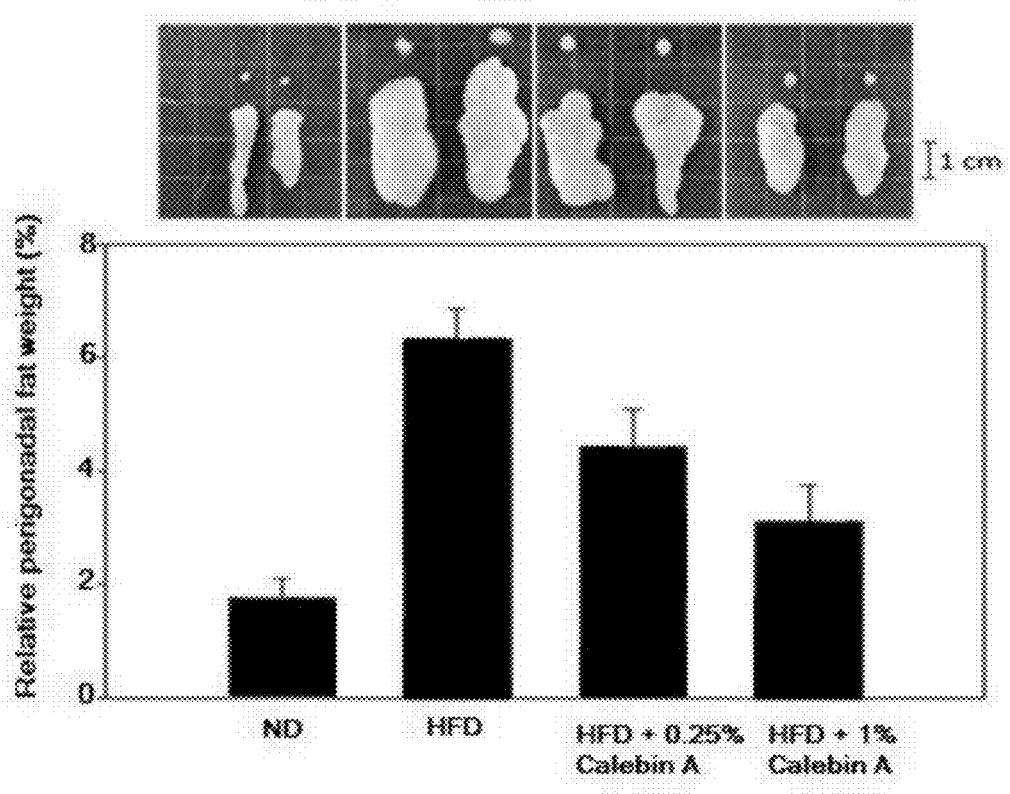
FIG. 10 (A), FIG. 10 (B) and FIG. 10 (C) show the effect of Calebin A supplementation on relative adipose tissue weights in High fat diet (HFD)-fed C57BL/6 mice.
Figure 10:
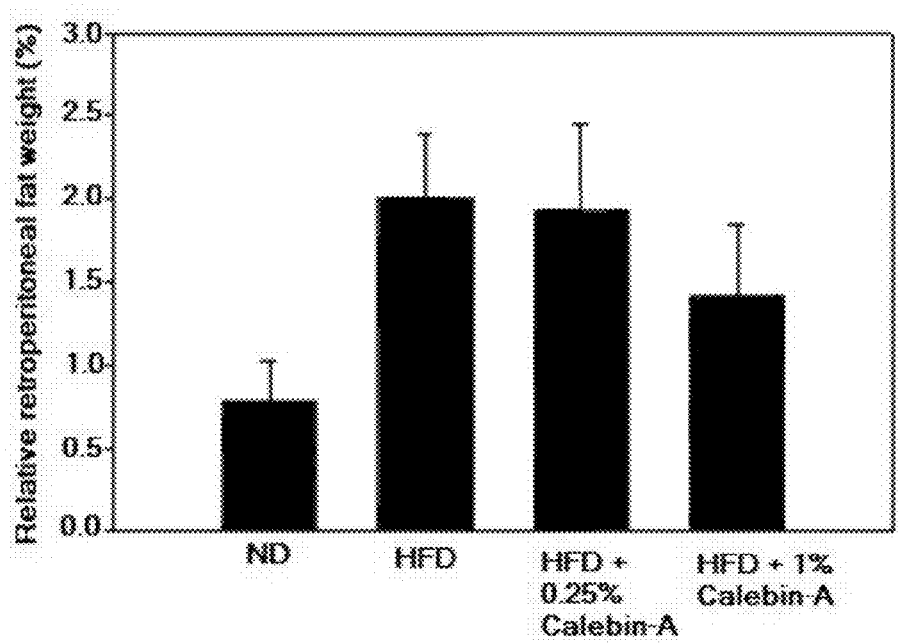
Figure 11:
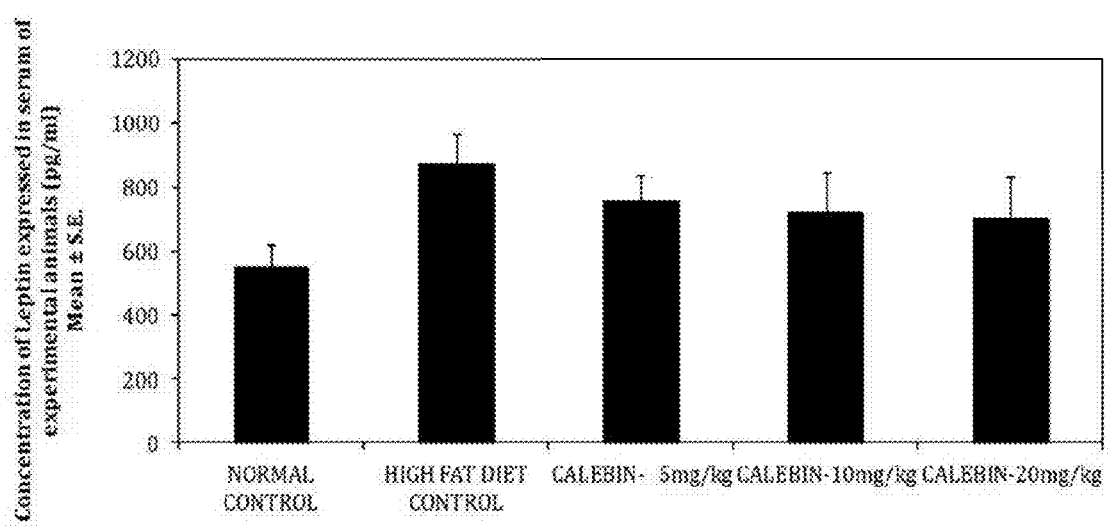
FIG. 11 shows the effect of Calebin A supplementation on leptin expression in the serum of C57BL/6 mice.

FIGS. 10 (A), (B) and (C) show the photographs of perigonadal fat, retroperitoneal and mesenteric fat and also the graphical representation of the % relative perigonadal, retroperitoneal and mesenteric fat weights.

TABLE IV

Composition of Experimental diets

| Composition/Ingredient | ND | HFD | HFD + 0.25% Calebin A | HFD + 1% Calebin A |
|---|---|---|---|---|
| Macronutrient Composition | | | | |
| Protein % of Energy | 20.0 | 14.0 | 14.0 | 14.0 |
| Carbohydrate % of Energy | 65.0 | 46.0 | 46.0 | 46.0 |
| Fat % of Energy | 15.0 | 40.0 | 40.0 | 40.0 |
| Ingredient g/kg | | | | |
| Lard | — | 150.0 | 150.0 | 150.0 |
| Soybean oil | — | 15.0 | 15.0 | 15.0 |
| Cholesterol | — | 1.0 | 1.0 | 1.0 |
| Calebin A | — | — | 2.5 | 10.0 |
| Energy Content kJ/g | 35.8 | 50.7 | 50.7 | 50.7 |

TABLE V

Effect of Calebin A on Body Weight Gain and Food Intake in Mice Fed HFD[a]

| Weight Parameters | ND | HFD | HFD + 0.25% Calebin A | HFD + 1% Calebin A |
|---|---|---|---|---|
| Initial wt (g) | 21.06 ± 0.99 | 22.13 ± 1.13 | 22.27 ± 0.49 | 21.88 ± 0.91 |
| Final wt (g) | 28.05 ± 1.08 | 38.63 ± 3.92*** | 35.28 ± 2.38 | 31.99 ± 2.50# |
| wt gain (g) | 6.99 ± 0.48 | 16.50 ± 2.90* | 13.02 ± 2.52 | 10.12 ± 2.48## |
| Food intake (g/mouse/day) | 4.35 ± 0.63 | 3.77 ± 0.52 | 3.57 ± 0.47 | 3.57 ± 0.40 |

[a]Mice were fed diet for 12 weeks as described under Materials and Methods, and the body weights were monitored twice weekly. The average body weight of each group is expressed as the mean ± SE (n = 8 per group), and statistical analysis was done by Student's t test. ND, normal diet; HFD, high-fat diet.
*P < 0.01, and
***P < 0.0001 compared with ND group.
P < 0.01, and
P < 0.001 compared with HFD group.

[a]Mice were fed diet for 12 weeks as described under Materials and Methods, and the body weights were monitored twice weekly. The average body weight of each group is expressed as the mean±SE (n=8 per group), and statistical analysis was done by Student's t test. ND, normal diet; HFD, high-fat diet. *, P<0.01, and ***, P<0.0001 compared with ND group. #, P<0.01, and ##P<0.001 compared with HFD group.

TABLE VI

Effects of Calebin A on relative organ weights in mice fed with HFD[a]

| Organ | ND | HFD | HFD + 0.25% Calebin A | HFD + 1% Calebin A |
|---|---|---|---|---|
| liver (%) | 3.86 ± 0.36 | 4.74 ± 0.66 | 4.05 ± 0.28 | 4.00 ± 0.25 |
| Kidney (%) | 1.30 ± 0.07 | 1.29 ± 0.23 | 1.22 ± 0.12 | 1.30 ± 0.15 |
| Spleen (%) | 0.20 ± 0.07 | 0.22 ± 0.09 | 0.16 ± 0.04 | 0.15 ± 0.04 |

[a]Mice were fed HFD supplemented with or without Calebin A (0.25 and 1%) for 12 weeks. Mice of each group were sacrificed at the end of week 12; the liver, spleen, and kidney were removed, photographed, weighed, and recorded. Data are presented as the mean ± SE (n = 8 per group). The relative organ weight is expressed as a percentage of body weight (liver weight/body weight × 100). ND, normal diet and HFD, high-fat diet.

[a]Mice were fed HFD supplemented with or without Calebin A (0.25 and 1%) for 12 weeks. Mice of each group were sacrificed at the end of week 12; the liver, spleen, and kidney were removed, photographed, weighed, and recorded. Data are presented as the mean±SE (n=8 per group). The relative organ weight is expressed as a percentage of body weight (liver weight/body weight×100). ND, normal diet and HFD, high-fat diet.

Animal Experiment—Study 2—Demonstration of Body Weight Loss in Obese Mammalian Models
Test System Details

| | |
|---|---|
| Animal species | Mice |
| Strain | C57 |
| Source | In-House |
| Body weight range | Males - 22.1-25.8 g |
| | Females - 20.3-23.9 g |
| Age at treatment | 8-10 weeks |
| Number of Groups | 5 groups (One Control, One High fat diet control and three treatment groups) |
| Number of animals/group | Each group consists of 10 animals (5 Males + 5 Females). Female animals used were nulliparous and non-pregnant |
| Total number of animals | 50 |
| Identification | Cage cards and individual animal ear notching method |

Test Performance
A. Husbandry
a. Conditions:
The animals were housed under standard laboratory conditions, air-conditioned with adequate fresh air supply (Air changes 12-15 per hour), room temperature 22±3° C., relative humidity 30-70%, with 12 hours light and 12 hours dark cycle. The temperature and relative humidity are recorded once daily.
b. Housing:
Individual animals were housed in a standard polypropylene cage (Size: L 290×B 140×H 140 mm) with stainless steel mesh top grill having facilities for holding pellet feed and drinking water in water bottle fitted with stainless steel sipper tube. Clean sterilized paddy husk is provided as bedding material.
c. Acclimatization:
The animals were acclimatized for 5 days to laboratory conditions and were observed for clinical signs daily.
d. Diet:
The animals were fed ad libitum with AMRUT Laboratory Animal Feed manufactured by Pranav Agro Industries Limited, Sangli, Maharastra throughout the acclimatization. Open Source Diet D12450B diet (with 10 kcal % Fat) and Open Source Diet D12492 High fat diet (with 60 kcal % Fat) manufactured by Research Diet Inc, USA procured from Indus Marketing, Hyderabad, Andhra Pradesh, INDIA was used for induction of obesity and the main study.
e. Water:
Clean drinking water was provided ad libitum throughout the acclimatization and obesity induction period. Deep borewell water passed through reverse osmosis unit was provided in plastic water bottles with stainless steel sipper tubes.

B. Grouping

Grouping of animals was done on the last day of acclimatization by body weight randomization and stratification method. Grouping of animals was done such that body weight variation of animals used does not exceed ±20% of the mean body weight of each group.

C. Study Design

The animals were divided into 5 groups viz., Group 1, 2, 3, 4 and 5 consisting of 10 animals (5 male and 5 female) each. The group details, doses and number/sex of animals per group are presented in Table VII.

TABLE VII

| Group | Treatment | Dose (mg/kg Bwt) | Number of Animals Male | Number of Animals Female | Animal numbers Male | Animal numbers Female |
|---|---|---|---|---|---|---|
| G1 | Control (with 10 kcal % Fat) | — | 5 | 5 | 1-5 | 26-30 |
| G2 | High fat diet Control (with 60 kcal % Fat) | — | 5 | 5 | 6-10 | 31-35 |
| G3 | Calebin A 5 mg/kg + High fat diet (with 60 kcal % Fat) | 5 | 5 | 5 | 11-15 | 36-40 |
| G4 | Calebin A 10 mg/kg + High fat diet (with 60 kcal % Fat) | 10 | 5 | 5 | 16-20 | 41-45 |
| G5 | Calebin A 20 mg/kg + High fat diet (with 60 kcal % Fat) | 20 | 5 | 5 | 21-25 | 46-50 |
| Total: | | | 25 | 25 | — | — |
| Total number of animals: | | | 50 | | | |

D. Animal Treatment a. Dose Volume:

Dose volume/animal=10 ml/kg body weight for all animals throughout the study period b. Obesity Induction:

The G1 Control group animals were fed with normal control diet feed D12450B containing 10 kcal % fat and the G2 to G5 group animals were fed with high fat diet feed D12492 containing 60 kcal % fat during the induction of obesity and during main study.

c. Main Study:

The main study was started after the induction of obesity. The 3 doses of Calebin A was administered to animals from Day 29 daily consecutively for a period of 28 days. The feeding of diets continued in the main study in a similar way as performed in induction of obesity. The G1 Control and G2 High fat diet control group animals were administered with 0.5% CMC (Carboxy Methyl Cellulose) while other group animals received test item from Day 29 to Day 56 of the study period. The dose volume of administration was maintained according to the weekly body weight of individual animals. The total duration of the study was 61 days (5 days Acclimatization period+28 days Induction of obesity+28 days Main study).

Statistical Analysis:

The raw data obtained from the present study were subjected to computer statistical processing. The computer printout of the data (in the form of appendix) was verified with the original raw data. After verification, the data was subjected to One-way ANOVA (Analysis of Variance) with Dunnett's post test for the data on body weights, hematology and clinical chemistry parameters, organ weights using GraphPad Prism version 5.01, GraphPad Software. All analyses and comparisons was evaluated at the 95% level of confidence (P<0.05), indicated by the designated by the superscripts of $a$ where G1 is compared to G3, G4, G5, and G6 and $b$ where G2 is compared to G3, G4, G5, and G6 throughout the report as stated below: *: Statistically significant (P<0.05) wherever applicable.

The data were subjected to One way—ANOVA statistical analysis by comparing the following:

G1 group {Control group (with 10 kcal % Fat)} to G3 group {Calebin A 5 mg/kg+High fat diet (with 60 kcal % Fat)}, G4 group {Calebin A–10 mg/kg+High fat diet (with 60 kcal % Fat)} and G5 group {Calebin A 20 mg/kg+High fat diet (with 60 kcal % Fat)} as represented below:

| G1 group | G3 group |
|---|---|
| Control group | Calebin A 5 mg/kg + |
| (with 10 kcal % Fat) | High fat diet (with 60 kcal % Fat) |
| | G4 group |
| | Calebin A -10 mg/kg + |
| | High fat diet (with 60 kcal % Fat) |
| | G5 group |
| | Calebin A 20 mg/kg + |
| | High fat diet (with 60 kcal % Fat) |

G2—High fat diet Control (with 60 kcal % Fat) to G3 group {Calebin A 5 mg/kg+High fat diet (with 60 kcal % Fat)}, G4 group {Calebin A–10 mg/kg+High fat diet (with 60 kcal % Fat)} and G5 group {Calebin A 20 mg/kg+High fat diet (with 60 kcal % Fat)} as represented below:

| G2 group | G3 group |
|---|---|
| High fat diet Control | Calebin A 5 mg/kg + |
| (with 60 kcal % Fat) | High fat diet (with 60 kcal % Fat) |
| | G4 group |
| | Calebin A -10 mg/kg + |
| | High fat diet (with 60 kcal % Fat) |
| | G5 group |
| | Calebin A 20 mg/kg + |
| | High fat diet (with 60 kcal % Fat) |

Results

Body Weight:

Individual animal body weights were recorded on the day of receipt on Day 1 and weekly (±1 day) thereafter during the study period.

The summary of weekly body weight of male and female animals is presented in Tables VIII (a)/VIII (b) and IX (a)/IX (b) respectively.

TABLE VIII (a)

| | | BODY WEIGHT (grams) | | | |
|---|---|---|---|---|---|
| | | DAYS | | | |
| GROUP | TREATMENT | 1 | 8 | 15 | 22 |
| G1[a] | Control (with 10 kcal % Fat) | 25.30 ± 1.49 | 26.12 ± 1.83 | 26.60 ± 2.03 | 26.86 ± 2.01 |
| G2[b] | High fat diet Control (with 60 kcal % Fat) | 25.20 ± 0.89 | 26.30 ± 1.44 | 28.22 ± 1.10 | 30.10 ± 1.44 |
| G3 | Calebin A 5 mg/kg + High fat diet | 25.02 ± 1.45 | 25.78 ± 1.14 | 27.68 ± 0.95 | 29.98**[a] ± 1.03 |
| G4 | Calebin A 10 mg/kg + High fat diet (with 60 kcal % Fat) | 25.28 ± 0.88 | 25.82 ± 0.91 | 27.58 ± 0.65 | 29.92**[a] ± 0.97 |
| G5 | Calebin A 20 mg/kg + High fat diet (with 60 kcal % Fat) | 25.88 ± 1.25 | 26.66 ± 1.73 | 28.94*[a] ± 1.59 | 30.64**[a] ± 1.16 | n = 5; Values are Mean ± Standard Deviation;
*Significant difference, P > 0.05

TABLE VIII

| | | BODY WEIGHT (grams) | | | | |
|---|---|---|---|---|---|---|
| | | DAYS | | | | |
| GROUP | TREATMENT | 29 | 36 | 43 | 50 | 56 |
| G1[a] | Control (with 10 kcal % Fat) | 27.26 ± 2.45 | 28.42 ± 3.09 | 28.64 ± 3.16 | 28.90 ± 3.35 | 29.26 ± 3.49 |
| G2[b] | High fat diet Control (with 60 kcal % Fat) | 31.72 ± 1.66 | 32.50 ± 1.47 | 33.90 ± 1.52 | 34.94 ± 1.19 | 35.96 ± 0.90 |
| G3 | Calebin A 5 mg/kg + High fat diet | 30.92***[a] ± 1.37 | 31.70*[a] ± 1.09 | 30.84****[b] ± 1.49 | 30.04****[b] ± 2.13 | 29.98***[b] ± 1.93 |
| G4 | Calebin A 10 mg/kg + High fat diet (with 60 kcal % Fat) | 31.02***[a] ± 0.70 | 31.06*[b] ± 1.55 | 29.80****[b] ± 1.48 | 28.98****[b] ± 1.10 | 28.62***[b] ± 1.18 |
| G5 | Calebin A 20 mg/kg + High fat diet (with 60 kcal % Fat) | 31.86****[a] ± 1.14 | 31.48*[b] ± 1.21 | 29.12**[b] ± 1.34 | 27.74[b] ± 1.28 | 27.54*[b] ± 1.87 | n = 5; Values are Mean ± Standard Deviation;
*Significant difference, P > 0.05

TABLE IX (a)

| | | BODY WEIGHT (grams) | | | |
|---|---|---|---|---|---|
| | | DAYS | | | |
| GROUP | TREATMENT | 1 | 8 | 15 | 22 |
| G1[a] | Control (with 10 kcal % Fat) | 23.18 ± 0.91 | 24.12 ± 1.21 | 24.68 ± 0.90 | 25.36 ± 0.80 |
| G2[b] | High fat diet Control (with 60 kcal % Fat) | 22.86 ± 1.05 | 23.82 ± 0.94 | 25.18 ± 1.00 | 26.48 ± 0.55 |
| G3 | Calebin A 5 mg/kg + High fat diet | 22.36 ± 0.65 | 23.18 ± 0.79 | 24.36 ± 0.87 | 25.66 ± 0.48 |
| G4 | Calebin A 10 mg/kg + High fat diet (with 60 kcal % Fat) | 23.16 ± 0.99 | 24.16 ± 1.29 | 25.62 ± 1.26 | 26.76 ± 1.27 |

TABLE IX (a)-continued

BODY WEIGHT (grams)

| GROUP | TREATMENT | DAYS | | | |
|---|---|---|---|---|---|
| | | 1 | 8 | 15 | 22 |
| G5 | Calebin A 20 mg/kg + High fat diet (with 60 kcal % Fat) | 23.52 ± 1.10 | 24.66 ± 1.24 | 26.26* $^a$ ± 1.05 | 27.26* $^a$ ± 1.25 | n = 5; Values are Mean ± Standard Deviation;
*Significant difference, P > 0.05

TABLE IX

BODY WEIGHT (grams)

| GROUP | TREAT-MENT | DAYS | | | | |
|---|---|---|---|---|---|---|
| | | 29 | 36 | 43 | 50 | 56 |
| G1$^a$ | Control (with 10 kcal % Fat) | 25.68 ± 0.79 | 26.28 ± 0.86 | 26.88 ± 0.83 | 27.52 ± 0.70 | 28.08 ± 0.73 |
| G2$^b$ | High fat diet Control (with 60 kcal % Fat) | 28.10 ± 0.42 | 29.14 ± 0.36 | 30.26 ± 0.63 | 32.00 ± 0.54 | 33.16 ± 0.36 |
| G3 | Calebin A 5 mg/kg + High fat diet | 27.40*$^a$ ± 0.60 | 28.18***$^a$ ± 0.68 | 28.46*$^a$,$^b$ ± 0.71 | 28.20*$^b$ ± 0.45 | 28.12***$^b$ ± 0.70 |
| G4 | Calebin A 10 mg/kg + High fat diet (with 60 kcal % Fat) | 28.46*$^a$ ± 1.10 | 28.64*$^a$ ± 0.62 | 28.16*$^a$,*$^b$ ± 0.36 | 27.54*$^b$ ± 0.38 | 27.04***$^b$ ± 0.47 |
| G5 | Calebin A 20 mg/kg + High fat diet (with 60 kcal % Fat) | 28.74*$^a$ ± 0.93 | 28.40$^a$ ± 1.03 | 27.80*$^b$ ± 0.99 | 27.44*$^b$ ± 0.95 | 27.10***$^b$ ± 0.93 | n = 5; Values are Mean ± Standard Deviation;
*Significant difference, P > 0.05

In male animals, there was statistically significant increase in mean weekly body weight values on Day 15 in G5 group {Calebin A-20 mg/kg+High fat diet (with 60 kcal % Fat)} compared to G1 group {Control group (with 10 kcal % Fat)}. These changes were considered to be related to difference in fat content of the feed.

In male animals, there was statistically significant increase in mean weekly body weight values on Day 22 and Day 29 in G3 group {Calebin A-5 mg/kg+High fat diet (with 60 kcal % Fat)}, G4 group {Calebin A-10 mg/kg+High fat diet (with 60 kcal % Fat)}, G5 group {Calebin A-20 mg/kg+High fat diet (with 60 kcal % Fat)} compared to G1 group {Control group (with 10 kcal % Fat)}. These changes were considered to be due to difference in fat content of the feed.

In male animals, there was statistical significant increase in mean weekly body weight values on Day 36 in 03 group {Calebin A-5 mg/kg+High fat diet (with 60 kcal % Fat)} compared to G1 group {Control group (with 10 kcal % Fat)}. These changes were considered to be due to difference in fat content of the feed.

In male animals, there was statistical significant decrease in mean weekly body weight values on Day 36 in G3 group {Calebin A-5 mg/kg+High fat diet (with 60 kcal % Fat)}, G4 group {Calebin A-10 mg/kg+High fat diet (with 60 kcal % Fat)} compared to G2 group {High fat diet Control (with 60 kcal % Fat)}. These changes were considered to be related to the effect of administration of test item Calebin A.

In male animals, there was statistical significant decrease in mean weekly body weight values on Day 43, 50 and Day 56 in G3 group {Calebin A-5 mg/kg+High fat diet (with 60 kcal % Fat)}, G4 group {Calebin A-10 mg/kg+High fat diet (with 60 kcal % Fat)}, G5 group {Calebin A-20 mg/kg+High fat diet (with 60 kcal % Fat)} compared to G2 group {High fat diet Control (with 60 kcal % Fat)}. These changes were considered to be due to administration of test item Calebin A.

In female animals, there was statistically significant increase in mean weekly body weight values on Day 15 and Day 22 in 05 group {Calebin A-20 mg/kg+High fat diet (with 60 kcal % Fat)} compared to G1 group {Control group (with 10 kcal % Fat)}. These changes were considered to be due to difference in fat content of the feed.

In female animals, there was statistically significant increase in mean weekly body weight values on Day 29 and Day 36 in G3 group {Calebin A-5 mg/kg+High fat diet (with 60 kcal % Fat)}, G4 group {Calebin A-10 mg/kg+High fat diet (with 60 kcal % Fat)}. G5 group {Calebin A-20 mg/kg+High fat diet (with 60 kcal % Fat)} compared to G1 group {Control group (with 10 kcal % Fat)}. These changes were considered to be due to difference in fat content of the feed.

In female animals, there was statistically significant increase in mean weekly body weight values on Day 43 in G3 group {Calebin A-5 mg/kg+High fat diet (with 60 kcal % Fat)}, G4 group {Calebin A-10 mg/kg+High fat diet (with 60 kcal % Fat)}, compared to G1 group {Control group (with 10 kcal % Fat)}. These changes were considered to be due to difference in fat content of the feed.

In female animals, there was statistically significant decrease in mean weekly body weight values on Day 43, 50 and Day 56 in G3 group {Calebin A-5 mg/kg+High fat diet (with 60 kcal % Fat)}, G4 group {Calebin A-10 mg/kg+High fat diet (with 60 kcal % Fat)}, G5 group {Calebin A-20 mg/kg+High fat diet (with 60 kcal % Fat)} compared to G2 group {High fat diet Control (with 60 kcal % Fat)}. These changes were considered to be due to administration of test item Calebin A.

It could thus be concluded that Calebin A had an effect in decreasing the body weights of high fat diet induced obese male and female C57 animals at test concentrations of 5, 10 and 20 mg/kg body weight.

Further, after completion of the study period (Day 57) the animals were humanely sacrificed by exposure to excess $CO_2$ in gas chamber and organ weights were noted. The brain, thymus, liver, adrenals, kidneys (paired), spleen, heart and ovaries/testes (paired) from all animals were trimmed off any adherent tissue, as appropriate and weighed wet as soon as possible to avoid drying. While in general, there was no statistically significant difference in organ weights in males and females, organ specific improvements in weight, example for liver in the male group was observable (See TABLE X). This result corroborates with those in TABLE VI for liver. It may be noted that Behnke, A. R. 1953. Lean body mass. A.M.A. Arch. Int. Med. 91, 585 indicates liver as an index of lean body mass promotion and H. F. Kraybill et al, J ANIM SCI 1954, 13:548-555 indicate that other visceral organs may also be equally predictive of lean body mass promotion. It is quite possible that statistical significance in terms of sustainable increase in organ weights without indications of toxicity may be achieved with a larger sample size (more number of tested animals) over extended testing periods. The results of Table VI and Table X may be interpreted as a preliminary indication of Calebin A's potential to not only inhibit adipogenesis and reduce body weight, but also promote to the lean body mass

TABLE X

| GROUP | TREATMENT | LIVER WEIGHT (g) |
|---|---|---|
| G1[a] | Control (with 10 kcal % Fat) | 1.47 ± 0.36 |
| G2[b] | High fat diet Control (with 60 kcal % Fat) | 1.60 ± 0.35 |
| G3 | Calebin A 5 mg/kg + High fat diet (with 60 kcal % Fat) | 1.41 ± 0.17 |
| G4 | Calebin A 10 mg/kg + High fat diet (with 60 kcal % Fat) | 1.25 ± 0.17 |
| G5 | Calebin A 20 mg/kg + High fat diet (with 60 kcal % Fat) | 1.79 ± 0.19 |

Figure 12:
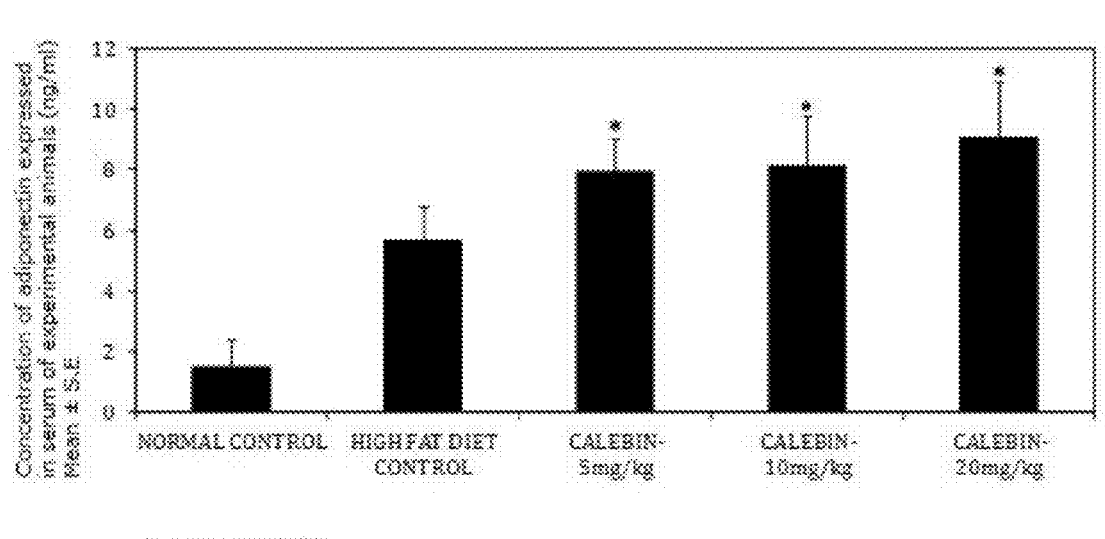
FIG. 12 shows the effect of Calebin A supplementation on adiponectin expression in the serum of C57BL/6 mice.

Further, on completion of the study period blood samples were collected from all the animals in tubes containing potassium ethylene di-amide tetra acetic acid (K2-EDTA) anticoagulant for estimation of systemic expression of leptin and adiponectin. Blood samples were collected humanely from retro-orbital plexus puncture method under mild ether anesthesia with the help of a fine capillary tube. The blood samples collected in tubes without anticoagulant were centrifuged at 3000 rpm for 10 minutes to obtain serum which was subjected to ELISA technique for the estimation of leptin and adiponectin. The import of leptin and adiponectin expression as biomarkers in obesity has been discussed in aforesaid paragraphs. Calebin A showed an insignificant effect on the inhibition of leptin expression in the serum of obese animals (FIG. 1) and showed a significant effect in enhancing the adiponectin expression in the serum levels of obese animals (FIG. 12). Low systemic adiponectin levels have been cited as predictive factors in the progression of disease states like Type II Diabetes mellitus (Chamukuttan Snehalatha et al, "Plasma Adiponectin Is an Independent Predictor of Type 2 Diabetes in Asian Indians", Diabetes Care December 2003 vol. 26 no. 12 3226-3229). The ability of Calebin A to significantly enhance the levels of systemic adiponectin in mammalian models of obesity indicates its ability to aid in preventing the onset of diabetes mellitus Type II in said mammals.

Calebin A and its Effect on Lipolysis and Lipocyte Size

Figure 13:
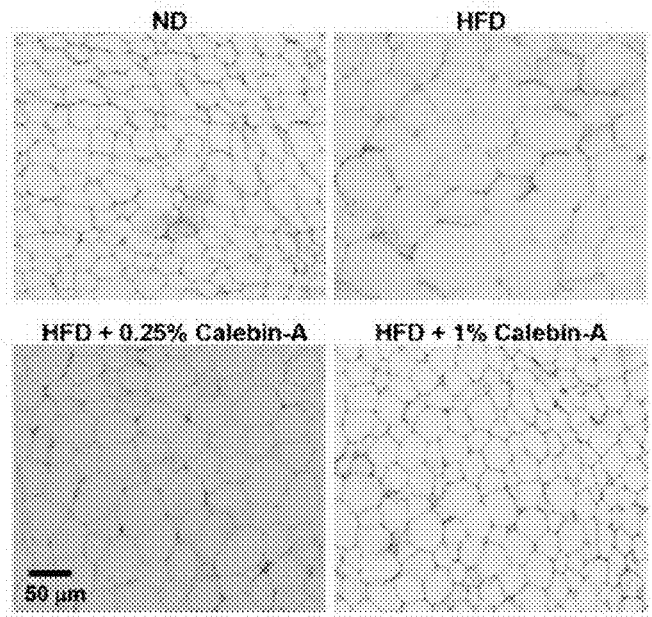
FIG. 13 (A) shows the H&E histological sections and FIG. 13 (B) the graphical representations thereof of the ability of Calebin A (0.25% and 1%) to restore adipocyte size in the HFD mice group.
Figure 13:
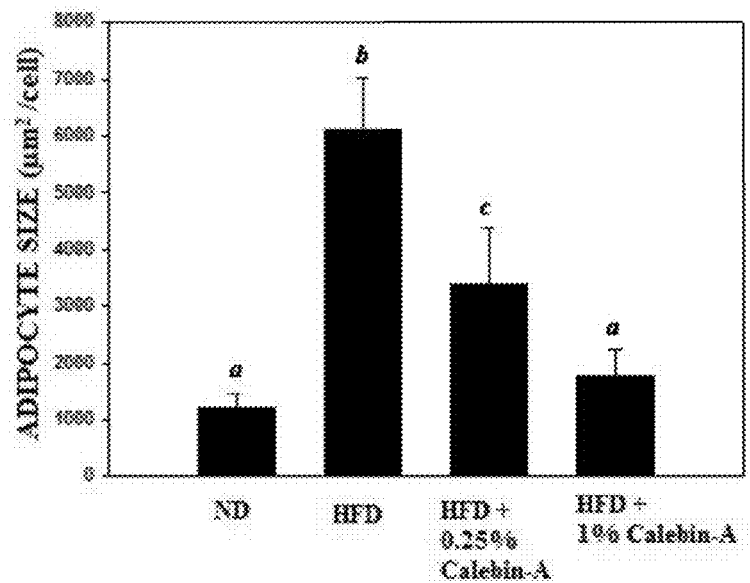

Fully differentiated adipocytes (8 days) previously untreated with Calebin A as described in procedural steps outlined in Example IV were treated with Calebin A at concentrations of 5-30 μM. Lipolysis was linked to the breakdown of lipids into glycerol that was released into the cell culture medium and detected thereof. It was observed that Calebin A at a concentration of 5-20 μM did not bring about the release of glycerol into the medium. Glycerol was detected when Calebin A at a concentration of 30 μM was used to treat adipocytes. Thus, in another most preferred embodiment, the present invention relates to a method of inducing lipolysis in mammalian adipocytes, said method comprising the step of treating mammalian adipocytes with varying concentrations of Calebin A to bring about the effect of dose dependant lipolysis in said adipocytes. Induction of obesity in Male C57BL/6J mice by treating with HFD for a period of 12 weeks as discussed in aforementioned paragraphs and evaluating histological sections of the epididymal fat (adipocytes) or in general fat connective tissue, showed a marked enlargement of adipocytes in size. Epididymal fat pads were dissected and fixed in 10% buffered formalin for at least 24 hours, then dehydrated with a sequence of ethanol solutions and processed for embedding in paraffin. Sections of 5-6 μm in thickness were cut, de-paraffinized, rehydrated, stained with haematoxylin & eosin (H&E) and subjected to photomicroscopic assessment. Adipocyte size was determined using a Nikon light microscope (Japan) equipped with an ocular micrometer at 200× magnification in 10 random fields per section. When the HFD mice were treated with Calebin A at concentrations of 0.25% and 1%, a remarkable reduction in the size of adipocytes was observed and adipocytes showed normal morphology (FIGS. 13 (A) and 13 (B)). Thus, in yet another most preferred embodiment, the present invention relates to a method of restoring adipocyte size in the fat tissue of obese mammals, said method comprising step of bringing into contact (a) enlarged mammalian adipocytes wherein enlargement resulting from a high fat diet regime, and (b) Calebin A derived through the oral administration of effective concentrations of Calebin A to said mammals, to achieve the effect of restoration of normal adipocyte size in fat tissue.

Figure 14:
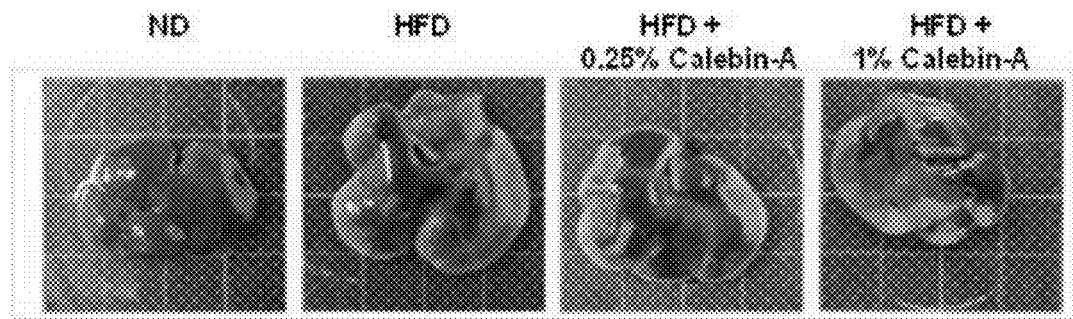
FIG. 14 (A) and FIG. 14 (B) respectively show the inflammation evident in the liver of the HFD group in the examination of gross morphology, inflammation with baloonic degeneration and triglyceride accumulation in the histological (H&E) sections, and the ability of Calebin A (025% and 1%) to reduce the inflammation, baloonic degeneration and triglyceride content in the liver.
Figure 14:
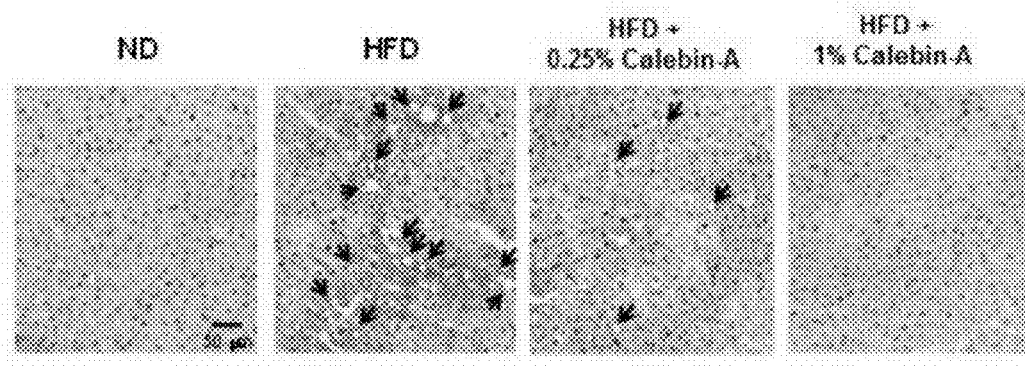
Figure 14:
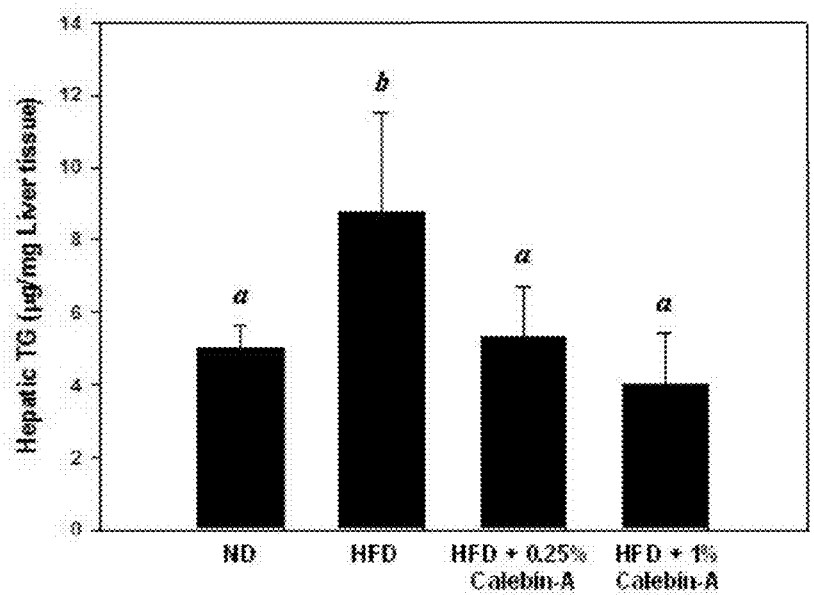

Calebin A and its effect on hepatic steatosis induced in mice fed with high fat diet (FIGS. 14 (A), 14 (B) and 14 (C))

C57BL/6J mice fed with HFD for period of 12 weeks were evaluated for serum levels of GOT and GTP. Results indicated enhanced serum GOT and GTP (TABLE XI) when compared to the ND group.

TABLE XI

|  | ND | HFD | HFD + 0.25% Calebin A | HFD + 1% Calebin A |
| --- | --- | --- | --- | --- |
| TCHO (mg/dl) | 117.00 ± 3.61$^a$ | 162.67 ± 15.89$^b$ | 136.50 ± 7.51$^c$ | 110.50 ± 17.97$^a$ |
| TG (mg/dl) | 144.33 ± 10.41$^a$ | 151.00 ± 8.89$^a$ | 121.25 ± 6.55$^b$ | 89.75 ± 5.85$^b$ |
| HDL (mg/dl) | 100.80 ± 7.95$^a$ | 109.40 ± 1.34$^a$ | 107.80 ± 2.05$^a$ | 104.50 ± 8.80$^a$ |
| GOT (U/l) | 120.33 ± 17.10$^a$ | 335.28 ± 18.80$^b$ | 110.33 ± 2.52$^b$ | 77.50 ± 11.12$^c$ |
| GPT (U/l) | 25.80 ± 6.91$^a$ | 38.25 ± 8.92$^b$ | 23.00 ± 2.92$^c$ | 32.50 ± 3.00$^a$ |

Data were presented as the mean±SE (n=8 per group). Mean values within each column with different labels (a,b,c) are significantly different (p<0.05) by one-way ANOVA and Duncan's Multiple Range Test. ND: normal diet; HFD: high fat diet.

Compared to the ND group, the liver of the HFD group was markedly enlarged as seen in gross morphological observation (HFD induced liver damage-hepatic steatosis). A portion of the livers in different groups were dissected and fixed in 10% buffered formalin for at least 24 hours, then dehydrated with a sequence of ethanol solutions and processed for embedding in paraffin. Sections of 5-6 μm in thickness were cut, deparaffinized, rehydrated, stained with haematoxylin & eosin (H&E) and subjected to photomicroscopic assessment. Liver histopathology was evaluated according to the NAFLD system outlined in Kleiner, D. E., Brunt, E. M., Van, N. M., Behling, C. et al., Design and validation of a histological scoring system for nonalcoholic fatty liver disease. *Hepatology* 2005, 41, 1313-1321. The score of hepatocellular ballooning was graded 0-2 based on the number of balloon cell per field at ×200 magnification (grading: 0=no balloon cell; 1=few balloon cells; 2=prominent balloon cells) in H&E stained sections. The number of infiltrating immune cells was counted at 200× magnification in five different areas. In the HFD group significant inflammatory degeneration, hepatocellular ballooning degeneration and triglyceride accumulation were seen. Quantitative analysis indicated elevated hepatic triglyceride levels as compared to the ND group. Administration of Calebin A at concentrations of 0.25% and 1% attenuated HFD induced triglyceride, hepatocellular ballooning degeneration and inflammatory infiltration in a dose dependant manner. Accordingly, in another most preferred embodiment, the present invention relates to a method of treating high fat diet (HFD) induced hepatic steatosis in mammals, said method comprising step of bringing into contact HFD affected hepatic cells marked by inflammatory infiltration, hepatocellular ballooning degeneration and high triglyceride levels with Calebin A derived from orally administering to said mammals effective concentrations of Calebin A to bring about the effect of attenuation of hepatic steatosis in a dose dependant manner. Alternatively, in another most preferred embodiment, the present invention also relates to Calebin A for treating high fat diet (HFD) induced hepatic steatosis in mammals.

While the invention has been described with reference to a preferred embodiment, it is to be clearly understood by those skilled in the art that the invention is not limited thereto. Rather, the scope of the invention is to be interpreted only in conjunction with the appended claims.

We claim:

1. A method of restoring adipocyte size in the fat tissue of obese mammals, said method comprising step of bringing into contact (a) enlarged mammalian adipocytes wherein enlargement resulting from a high fat diet regime, and (b) Calebin-A by orally administering effective concentrations of Calebin-A to said mammals, to achieve the effect of restoration of normal adipocyte size in fat tissue.

2. A method of treating high fat diet (HFD) induced hepatic steatosis in mammals, said method comprising step of bringing into contact HFD affected hepatic cells marked by inflammatory infiltration, hepatocellular ballooning degeneration and high triglyceride levels with Calebin-A by orally administering to said mammals effective concentrations of Calebin-A to bring about the effect of attenuation of hepatic steatosis in a dose dependant manner.

* * * * *